United States Patent [19]

Ohsaka et al.

[11] Patent Number: 4,719,052
[45] Date of Patent: Jan. 12, 1988

[54] 2,2-DIFLUOROPROPIONIC ACID DERIVATIVES

[75] Inventors: Yohnosuke Ohsaka; Takashi Tohzuka; Shoji Takaki; Yoshio Negishi; Satoru Kohno, all of Osaka, Japan

[73] Assignee: Daikin Industries Ltd., Osaka, Japan

[21] Appl. No.: 684,344

[22] Filed: Dec. 20, 1984

[30] Foreign Application Priority Data

Dec. 26, 1983 [JP] Japan ................. 58-251070
Nov. 29, 1984 [JP] Japan ................. 59-253884

[51] Int. Cl.$^4$ ............................................. C07C 53/18
[52] U.S. Cl. .............................. 260/544 F; 260/544 G; 560/145; 560/184; 560/227
[58] Field of Search .................. 260/544 F, 544 G; 560/184, 227, 145

[56] References Cited

U.S. PATENT DOCUMENTS 2,010,154  8/1935  Hubacher ............................ 560/187
2,678,953  5/1954  Conly ................................. 560/227
3,950,160  4/1976  El-Haj et al. ........................ 71/92

OTHER PUBLICATIONS

Chuvatkin, N. N. et al., *Chemical Abstracts*, vol. 97 (1982) #144272r.

*Primary Examiner*—Werren B. Lone
*Assistant Examiner*—L. Hendriksen
*Attorney, Agent, or Firm*—Birch, Stewart, Kolasch & Birch

[57] ABSTRACT

2,2,3-trifluoropropionyl fluoride is prepared by opening the ring of tetrafluorooxetane in the presence of a catalyst. Analogously, a novel 2,2-difluoropropionic acid derivative of the formula:

$$XCH_2CF_2COY \qquad (I)$$

wherein X is chlorine, bromine, iodine, a group of the formula:

$$R_1O— \qquad (II)$$

or $$R_2COO— \qquad (III)$$

wherein $R_1$ $R_2$ are each an aliphaic or halogenated aliphatic hydrocarbon group having 1 to 8 carbon atoms or an aromatic hydrocarbon group having 6 to 8 carbon atoms optionally bearing at least one substituent, or a group of the formula:

$$X'CH_2CF_2CF_2O— \qquad (IV)$$

wherein X' is fluorine, chlorine, bromine, iodine, the group of the formula: $R_1O—$ or $R_2COO—$; and Y is fluorine or a group of the formula:

$$—OR_3 \qquad (V)$$

wherein $R_3$ is an aliphatic or halogenated aliphatic hydrocarbon group having 1 to 8 carbon atoms except a perfluorohydrocarbon group or an aromatic hydrocarbon group having 6 to 8 carbon atoms optionally bearing at least one substituent or of the formula :

$$—OCH_2R_f \qquad (V')$$

wherein $R_f$ is an aliphatic perfluorohydrocarbon having 1 to 7 carbon atoms is prepared.

7 Claims, No Drawings

2,2-DIFLUOROPROPIONIC ACID DERIVATIVES

FIELD OF THE INVENTION

The present invention relates to 2,2-difluoropropionic acid derivatives. More particularly, it relates to 2,2-difluoropropionic acid derivatives and a process for preparing the same from 2,2,3,3-tetrafluorooxetane (hereinafter referred to as "tetrafluorooxetane").

BACKGROUND OF THE INVENTION 2,2,3-Trifluoropropionyl fluoride is useful as an intermediate for the production of medicines and agricultural chemicals and as a strong acid catalyst. Further, its ester derivative is useful as a solvent, and its dehydrogenated fluorinated derivative is useful as a monomer. It is known that it can be obtained as one of many products prepared by fluorinating propionyl chloride with fluorine in the presence of a cobalt fluoride catalyst (cf. J. C. Tatlow et al, J. of Fluorine Chemistry, 1973 (3), 329–30).

SUMMARY OF THE INVENTION

One object of the present invention is to provide a novel process for preparing 2,2,3-trifluoropropionyl fluoride.

Another object of the present invention is to provide novel 2,2-difluoropropionic acid derivatives.

DETAILED DESCRIPTION OF THE INVENTION

According to the present invention, 2,2,3-trifluoropropionyl fluoride is prepared by conducting a ring opening reaction of tetrafluorooxetane in the presence of a catalyst.

Tetrafluorooxetane is a known compound and easily synthesized by reacting tetrafluoroethylene and formaldehyde.

Specific examples of the catalyst to be used in the above reaction are alkali metal fluorides and Lewis acids.

Preferred alkali metal fluorides are sodium fluoride, potassium fluoride and cesium fluoride, and preferred Lewis acids are $AlCl_3$ and $SbF_5$.

The above reaction may be carried out either in a liquid phase or in a gaseous phase.

When the reaction is carried out in the liquid phase, the alkali metal fluoride is dissolved in an aprotic solvent (eg. diglyme, tetraglyme, acetonitrile, etc.), and thereto tetrafluorooxetane is added.

The reaction temperature is usually from 80° C. to the boiling point of the solvent, preferably from 80° to 200° C. The reaction time depends on the reaction temperature, the kind and amount of the catalyst, and is preferably from 1 to 24 hours.

In the liquid phase reaction, preferred catalysts are potassium fluoride and cesium fluoride. The amount of the catalyst is at least a catalytic amount and preferably from 1 to 50% by mole based on tetrafluorooxetane.

In the case of the gaseous phase reaction, when the alkali metal fluoride is used as the catalyst, the reaction temperature is not higher than 500° C., preferably from 200° to 450° C. At a temperature higher than 500° C., tetrafluorooxetane is decomposed. The reaction pressure may be atmospheric pressure or a pressure higher or lower than atmospheric pressure as long as the reaction system is kept in a gaseous state. The space velocity depends on other reaction conditions such as the temperature, pressure, the kind and amount of the catalyst, and preferably from 10 to 1,000 $hr^{-1}$. The raw material may be diluted with an inactive gas such as nitrogen.

In the gaseous phase reaction, the catalyst is supported on a carrier (eg. activated carbon, asbestos, nickel oxide, silica gel, molecular sieve, etc.). Among them, activated carbon is preferred.

When the Lewis acid is used as the catalyst, it may be dissoled in a solvent (eg. $CH_2Cl_2$, $CHCl_3$, $CCl_4$, etc.). $SdF_5$ does not necessarily require any solvent. The reaction temperature is usually from room temperature to 50° C.

If tetrafluorooxetane is analogously ring opened in the presence of an appropriate coreactant, a novel 2,2-difluoropropionic acid derivative is prepared.

The novel 2,2-difluoropropionic acid derivative of the invention is represented by the formula:

$$XCH_2CF_2COY \qquad (I)$$

wherein X is chlorine, bromine, iodine, a group of the formula:

$$R_1O— \qquad (II)$$

or $$R_2COO— \qquad (III)$$

wherein $R_1$ and $R_2$ are each an aliphatic or halogenated aliphatic hydrocarbon group having 1 to 8 carbon atoms or an aromatic hydrocarbon group having 6 to 8 carbon atoms optionally bearing at least one substituent, or a group of the formula:

$$X'CH_2CF_2CF_2O— \qquad (IV)$$

wherein X' is flourine, chlorine, bromine, iodine, the group of the formula: $R_1O—$ or $R_2COO—$; and Y is fluorine, a group of the formula:

$$—OR_3 \qquad (V)$$

wherein $R_3$ is an aliphatic or halogenated aliphatic hydrocarbon group having 1 to 8 carbon atoms, except a perfluorohydrocarbon group, or an aromatic hydrocarbon group having 6 to 8 carbon atoms optionally bearing at least one substituent, or a group of the formula:

$$—OCH_2R_f \qquad (V')$$

wherein $R_f$ is an aliphatic perfluorohydrocarbon having 1 to 7 carbon atoms.

Specific examples of the aliphatic or halogenated aliphatic hydrocarbon of perfluorohydrocarbon group are methyl, ethyl, propyl, trifluoromethyl, 2,2,3,3,3-pentafluoropropyl, perfluoropropyl, perfluro(2-propoxy-2-methylethyl), etc. Specific examples of the aromatic hydrocarbon group are phenyl, toluyl, trifluoromethylphenyl, chlorophenyl, bromophenyl, etc.

The derivative (I) wherein Y is fluorine may be prepared by reacting tetrafluorooxetane with a material by which X is introduced in the derivative (eg. alkali metal halides).

The derivative (I) wherein Y is the group of the formula: $—OR_3$ or $—OCH_2R_f$ may be prepared by reacting tetrafluorooxetane with an alcohol or phenol of the formula:

$$R_3OH \text{ or } R_fCH_2OH \tag{VI}$$

wherein $R_3$ and $R_f$ are the same as defined above in the presence of the material by which X is introduced in the derivative.

Specific examples of the alkali metal halides are sodium bromide, potassium iodide, potassium bromide, and potassium chloride. The group (II) may be introduced by a mixture of a corresponding alcohol of the formula:

$$R_1OH \tag{VI}$$

wherein $R_1$ is the same as defined above and an alkali metal halide or an alcoholate of the alcohol (VI). The group (III) may be introduced by alkali metal salts (eg. sodium or potassium salt) of a corresponding acid. The group (IV) is preferably introduced by a compound of the formula:

$$FCH_2CF_2COF \text{ or } XCH_2CF_2COF \tag{VII}$$

wherein X is the same as defined above.

The above reaction may be carried out in a solvent, specific examples of which are the above-described aprotic solvents, ethers and benzene.

The reaction temperature is usually from 0° C. to a refluxing temperature of the solvent and preferably not higher than a temperature to which the reaction mixture is heated by the reaction heat.

The novel 2,2-difluoropropionic acid derivative of the present invention is useful as a solvent, a catalyst, a monomer, etc.

The present invention will be explained further in detail by following Examples.

EXAMPLE 1

In a 100 ml stainless steel autoclave, diglyme (15 ml), potassium fluoride (1.8 g) and tetrafluorooxetane (13 g, 0.10 mole) were charged and stirred at 150° C. for 8 hours. A mixture of products (12.8 g) and the unreacted raw material were recovered by distillation. The product mixture was analyzed by GLC, IR, MS and NMR to find that it contained 65% by mole of 2,2,3-trifluoropropionyl fluoride.

EXAMPLE 2

Activated carbon pellets each having a diameter of 4 mm and a length of 6 mm were immersed in an aqueous solution of potassium fluoride and dried to produce a potassium fluoride catalyst supported on activated carbon in an amount of 30% by weight based on the weight of carbon.

The thus produced catalyst pellets (50 ml) were filled in a ¾ inch Hastelloy-C tube and the interior temperature was kept at 380° C. Then, tetrafluorooxetane (30 g) carried by nitrogen was passed through the reactor over 30 minutes. The exit gas was trapped by a trap cooled by dry ice. The trapped material (29.5 g) contained 99.3% by mole of 2,2,3-trifluoropropionyl fluoride and a trace amount of the unreacted raw material according to GLC analysis.

EXAMPLE 3

In a 300 ml flask equipped with a dry ice condenser and a dropping funnel, carbon tetrachloride (100 ml) and aluminum chloride (5.0 g) were charged and stirred. Then, tetrafluorooxetane (150 ml) was dropwise added and stirred for about 2 hours. After cooling, the reaction mixture was rectified to give 2,2,3-trifluoropropionyl fluoride (125 g).

EXAMPLE 4

In a 50 ml flask equipped with a dry ice condenser and a dropping funnel, $SbF_5$ (5.0 g) was added and then tetrafluorooxetane (30.0 g) was dropwise added with stirring. After the termination of reflux, the reaction mixture was rectified to give 2,2,3-trifluoropropionyl fluoride (23.5 g).

EXAMPLE 5

In a 300 ml three-necked flask, the sodium bromide (40 g, 0.39 mole) and diglyme (100 ml) which was dehydrated by molecule sieve were charged. After a condenser was attached to the top of the flask, tetrafluorooxetane (30 ml, 0.32 mole) which was dehydrated by molecular sieve was dropwise added over about 30 minutes with stirring on an ice bath. After addition, the reaction was further continued at room temperature for about 2 and a half hours. Consumption of tetrafluorooxetane was confirmed by GC.

The reaction mixture was distilled under atmospheric pressure to obtain $BrCH_2CF_2COF$ (42 g). B.P. 73° C. Yield, 67%. The results of IR and MS are as follows:

IR: 3,000 cm$^{-1}$ (C—H, stretching), 1,890 cm$^{-1}$ (C=O, stretching), 1,430 cm$^{-1}$, 1,330 cm$^{-1}$, 1,230 cm$^{-1}$, 1,140 cm$^{-1}$, 1,100 cm$^{-1}$ and 1,040 cm$^{-1}$.

MS: m/e=192 (M+2, 8.9%), 190 (M, 9.6%), 125 (21%), 123 (21%), 83 (44%), 64 (100%) and 47 (54%).

EXAMPLE 6

In a 300 ml three-necked flask, a 23 wt. % solution of sodium methylate in methanol was charged and then tetrafluorooxetane (30 ml) was dropwise added on an ice bath. Since tetrafluorooxetane vigorously reacted as it was added, it was gradually added over about 1 hour. The top of the flask was attached with an ice cooled condenser.

After addition, the reaction was continued at room temperature for another 1 hour. Termination of reaction was confirmed by disappearance of the tetrafluorooxetane peak in GC.

After removing methanol from the reaction mixture, the residue was poured in water (200 ml) and extracted with ether (300 ml).

After distilling off ether from the extract under atmospheric pressure, the residue was distilled under a reduced pressure to give $CH_3OCH_2CF_2COOCH_3$ (23.4 g) at 58°–9° C./40 mmHg. Yield, 47.5%.

IR: 3,600 cm$^{-1}$ (C—H), 1,790 cm$^{-1}$ (C=O), 1,450 cm$^{-1}$, 1,350–1,050 cm$^{-1}$ (broad), 950 cm$^{-1}$ and 840 cm$^{-1}$.

MS: m/e=155 (M+1, 0.4%), 134 (4.9%), 45 (100%), 29 (25%) and 15 (31%).

EXAMPLE 7

In a three-necked flask, sodium hydride (7.68 g, 0.32 mole) and monoglyme (100 ml) were charged. The flask was equipped with a condenser and cooled by ice. Then, 2,2,3,3,3-pentafluoropropanol (48 g, 0.32 mole) was dropwise added. During addition, hydrogen was vigorously generated. After termination of hydrogen generation, tetrafluorooxetane (15 ml, 0.16 mole) was dropwise added over about 30 minutes. Thereafter, the solution became so viscous that it was difficult to stir.

The solution was poured in water (300 ml) and the lower organic layer was recovered. After distilling off monoglyme under atmospheric pressure, it was distilled under reduced pressure to give $CF_3CF_2CH_2OCH_2CF_2COOCH_2CF_2CF_3$ (35.2 g) at 66°–68° C./11 mmHg. Yield, 28%.

IR: 3,000 cm$^{-1}$ (C—H), 1,800 cm$^{-1}$ (C=O), 1,450 cm$^{-1}$ and 1,400–950 cm$^{-1}$ (broad).

$^{19}$F-NMR (ppm): 7.6 (d, 6F), 36.6 (t, 2F) and 47.1 (s, 4F).

$^1$H—NMR: δ(ppm) = 4.8 (t, 2H),
4.12 (t, 2H)
4.1 (t, 2H) } overlapping.

EXAMPLE 8

To a suspension of sodium hydride (2.17 g, 0.057 mole) in monoglyme (10 ml) cooled on an ice bath, a solution of phenol in monoglyme was dropwise added with stirring. After termination of hydrogen generation, tetrafluorooxetane (2.6 g, 0.02 mole) was dropwise added. Thereafter, the temperature of the bath was raised to 50° C. and at the same temperature, the reaction was further continued for about 4 hours. In the course of the reaction, when the mixture became too viscous, it was diluted by monoglyme. Termination of the reaction was confirmed by disappearance of the tetrafluorooxetane peak in GC.

In TLC (developer, benzene:ethyl acetate=10:1), a spot of the product was found at $R_f$=0.9 (spot for phenol at $R_f$=0.8).

The reaction mixture was poured in water, and the lower organic layer was recovered and washed three times with 5 times volume. From the organic layer,

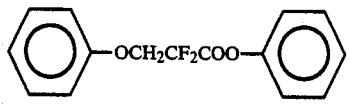

was obtained.

IR: 3,100 cm$^{-1}$ (aromatic C—H), 2,950 cm$^{-1}$ (C—H), 1,780 cm$^{-1}$ (C=O), 1,590 cm$^{-1}$, 1,460 cm$^{-1}$, 1,400–1,000 cm$^{-1}$ (broad), 950 cm$^{-1}$, 920 cm$^{-1}$, 830 cm$^{-1}$ and 750 cm$^{-1}$.

$^1$H-NMR (in CDCl$_3$): δ(ppm)=4.46 (t, 2H) and 7.2 (m, 10H).

EXAMPLE 9

To a mixture of sodium iodide (825 g, 5.5 moles) and tetraglyme (1.5 l), tetrafluorooxetane (650 g, 5 moles) was dropwise added with stirring. After addition, the reaction mixture was further stirred for about 2 hours and then distilled under reduced pressure to give 2,2-difluoro-3-iodopropionyl fluoride (1,128 g). B.P. 35° C./95 mmHg. Yield, 94%.

MS: m/e=238 (M$^+$, 100%), 191 (33%), 127 (30%) and 64 (50%).

EXAMPLE 10

To a mixture of potassium iodide (83 g, 0.5 mole) and tetraglyme (10 ml), tetrafluorooxetane (90 ml, 1 mole) was dropwise added with stirring. After addition, the reaction mixture was further stirred overnight and kept standing for several days. Thereafter, the supernatant was recovered by decantation and distilled under reduced pressure to give ICH$_2$CF$_2$COF (60 ml, 107 g) at about 35° C./95 mmHg and ICH$_2$CF$_2$CF$_2$CH$_2$CF$_2$COF (20 ml, 32 g) at 91°–96° C./19 mmHg.

MS: m/e=368 (M$^+$, 100%), 271 (7%), 241 (35%), 191 (42%), 111 (69%), 95 (38%), 83 (88%) and 64 (46%).

$^{19}$F-NMR (in tetraglyme) (ppm): −93.4 (br, COF), 11.0 (s, CF$_2$O), 32.2 (tt, CF$_2$CO) and 35.9 (q, CH$_2$CF$_2$CF$_2$).

EXAMPLE 11

To a mixture of potassium bromide (6.6 g, 0.055 mole) and tetraglyme (20 ml), tetrafluorooxetane (10 ml, 0.11 mole) was dropwise added with stirring. After addition, the reaction mixture was further stirred for about 4 hours and kept standing overnight. The reaction mixture did not separate but was diluted with tetraglyme and analyzed to give following results:

$^{19}$F-NMR (in tetraglyme) (ppm): BrCH$_2$CF$_2$COF: −92 (br, COF) and 25.2 (t, CF$_2$). BrCH$_2$CF$_2$CF$_2$OCH$_2$CF$_2$COF: −91.2 (br, COF), 10.7 (s, CF$_2$O), 33.6 (t, CF$_2$CO) and 36.4 (tt, CH$_2$CF$_2$CF$_2$).

EXAMPLE 12

To a mixture of potassium chloride (5 g, 0.066 mole), tetrabutylammonium hydrogensulfate (0.1 g) and diglyme (20 ml), tetrafluorooxetane (4 ml, 0.044 mole) was dropwise added with stirring. After addition, the reaction mixture was further stirred for 3 hours and kept standing overnight. A part of the supernatant was analyzed by $^{19}$F-NMR and the remaining part was distilled under reduced pressure. The products having low boiling temperatures were trapped by a trap cooled with liquid oxygen and analyzed by GC-MS.

$^{19}$F-NMR (in diglyme) (ppm): ClCH$_2$CF$_2$COF: −97.9 (br, COF) and 30.2 (t, CF$_2$). ClCH$_2$CF$_2$CF$_2$OCH$_2$CF$_2$COF: −97.9 (br, COF), 11.2 (s, CF$_2$O), 35.6 (t, CF$_2$CO) and 42.1 (tt, CH$_2$CF$_2$CF$_2$).

EXAMPLE 13

To a mixture of glyme (10 ml) and sodium hydride (4.33 g, 0.118 mole) which was washed with a small amount of dry glyme three times, a mixture of trifluoroacetic acid (12.5 g, 0.110 mole) and glyme (10 ml) was dropwise added. After addition of the latter mixture and termination of hydrogen generation, tetrafluorooxetane (9.6 ml, 0.106 mole) was dropwise added. Thereafter, the reaction mixture was stirred overnight and then kept standing for a while. A part of the supernatant was analyzed by $^{19}$F-NMR and GC-MS and the remaining part was distilled under reduced pressure. Volatile materials were trapped with a trap cooled by a dry ice-methanol bath. The trapped materials were fractioned under atmospheric pressure and separated into those distilled at 75° C. or lower, those distilled at 80° C. or higher and the hold-up (the bath temperature of about 100° C.). In the hold-up, CF$_3$COOCH$_2$CF$_2$COF and CF$_3$COOCH$_2$CF$_2$CF$_2$OCH$_2$CF$_2$COF were concentrated.

CF$_3$COOCH$_2$CF$_2$COF

IR: 1,900 cm$^{-1}$ and 1,880 cm$^{-1}$ (—COF), and 1,820 cm$^{-1}$ (—COO—).

MS: m/e=205 (M$^+$-F, 0.3%), 185 (0.5%), 177 (18%), 127 (46%), 111 (100%), 99 (49%), 83 (95%) and 69 (92%).

$^{19}$F-NMR (ppm): −96.8 (t, COF), −2.0 (s, CF$_3$) and 35.8 from TFA (td, CF$_2$).

CF₃COOCH₂CF₂CF₂OCH₂CF₂COF

MS: m/e=313 (M⁺-F, 0.2%), 285 (2.5%), 219 (11%), 205 (7%), 177 (68%), 127 (9%), 111 (82%), 83 (95%), 69 (100%) and 64 (61%).

¹⁹F-NMR (ppm): −96.8 (s, COF), −1.1 (s, CF₃), 2.3 (s, CF₂O), 36.4 (t, CF₂CO) and 42.0 from TFA (t, CH₂CF₂CF₂).

EXAMPLE 14

In a 500 ml flask, tetraglyme (200 ml), cesium fluoride (5.0 g, 0.03 mole) and hexafluoropropyleneoxide dimer (100 g, 0.30 mole) were charged. To the mixture on a bath kept at 20° C. tetrafluorooxetane (50.0 g, 0.38 mole) was dropwise added. Thereafter, the reaction mixture was stirred for 5 hours and distilled under atmospheric pressure to give C₃F₇OCF(CF₃)CF₂OCH₂CF₂COF (53 g) at 140° C. d=1.67 (25° C.).

| Elemental analysis: | C | H | F |
|---|---|---|---|
| Calc'd: | 23.6% | 0.4% | 65.9% |
| Found: | 23.4% | 0.4% | 65.8% |

What is claimed is:

1. A 2,2-difluoropropionic acid derivative of the formula:

XCH₂CF₂COY wherein X is bromine, iodine, a group of the formula:

R₁O— or

R₂COO— wherein R₁ and R₂ are each an aliphatic or halogenated aliphatic hydrocarbon group having 1 to 8 carbon atoms or an aromatic hydrocarbon group selected from the group consisting of phenyl, toluyl, trifluoromethylphenyl, chlorophenyl, and bromophenyl, or a group of the formula:

X'CH₂CF₂CF₂O— wherein X' is fluorine, chlorine, bromine, iodine, the group of the formula: R₁O— and R₂COO—; and Y is fluorine.

2. A derivative according to claim 1, wherein X is selected from the group consisting of bromine and iodine.

3. A derivative according to claim 1, wherein X is the group of the formula:

R₁O—          (II)

or

R₂COO—          (III).

4. A derivative according to claim 1, wherein X is a group of the formula:

X'CH₂CF₂CF₂O—          (IV).

5. A 2,2-difluoropropionic acid derivative of the formula:

XCH₂CF₂COY wherein X is X'CH₂CF₂CF₂O— wherein X' is fluorine, chlorine, bromine, iodine, the group of the formula: R₁O— or R₂COO—, wherein R₁ and R₂ are each an aliphatic or halogenated aliphatic hydrocarbon group having 1 to 8 carbon atoms or an aromatic hydrocarbon group selected from the group consisting of phenyl, toluyl, trifluoromethylphenyl, chlorophenyl, and bromophenyl, and Y is fluorine or a group of the formula:

—OR₃ wherein R₃ is an aliphatic or halogenated aliphatic hydrocarbon group having 1 to 8 carbon atoms, except a perfluorohydrocarbon group, or an aromatic hydrocarbon group selected from the group consisting of phenyl, toluyl, trifluoromethylphenyl, chlorophenyl, and bromophenyl, or a group of the formula:

—OCH₂R_f wherein R_f is an aliphatic perfluorohydrocarbon having 1 to 7 carbon atoms.

6. A derivative according to claim 5, wherein Y is fluorine.

7. A derivative according to claim 5, wherein Y is —OR₃ or —OCH₂R_f.

* * * * *